(12) United States Patent
Metzger (10) Patent No.: US 8,617,250 B2
(45) Date of Patent: Dec. 31, 2013

(54) REVISION KNEE TIBIAL LOCKING MECHANISM

(75) Inventor: Robert Metzger, Wakarusa, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 112 days.

(21) Appl. No.: 13/162,789

(22) Filed: Jun. 17, 2011

(65) Prior Publication Data

US 2012/0323333 A1    Dec. 20, 2012

(51) Int. Cl.
*A61F 2/38* (2006.01)

(52) U.S. Cl.
USPC .................................................. 623/20.32

(58) Field of Classification Search
USPC .......... 623/20.26–20.28, 20.14–20.15, 20.33, 623/20.29
See application file for complete search history.

(56) References Cited

U.S. PATENT DOCUMENTS

| | | | | |
|---|---|---|---|---|
| 4,257,129 A * | 3/1981 | Volz | | 623/20.33 |
| 4,714,474 A * | 12/1987 | Brooks et al. | | 623/20.33 |
| 4,731,087 A * | 3/1988 | Sculco et al. | | 623/21.15 |
| 4,936,853 A * | 6/1990 | Fabian et al. | | 623/20.15 |
| 4,938,769 A * | 7/1990 | Shaw | | 623/20.15 |
| 4,944,757 A * | 7/1990 | Martinez et al. | | 623/20.15 |
| 5,080,675 A * | 1/1992 | Lawes et al. | | 623/20.33 |
| 5,108,442 A * | 4/1992 | Smith | | 623/20.33 |
| 5,194,066 A * | 3/1993 | Van Zile | | 623/20.15 |
| 5,201,881 A * | 4/1993 | Evans | | 623/20.28 |
| 5,282,868 A * | 2/1994 | Bahler | | 623/20.29 |
| 5,330,534 A * | 7/1994 | Herrington et al. | | 623/20.27 |
| 5,344,460 A * | 9/1994 | Turanyi et al. | | 623/20.33 |
| 5,387,240 A * | 2/1995 | Pottenger et al. | | 623/20.29 |
| 5,413,608 A * | 5/1995 | Keller | | 623/20.33 |
| 5,702,464 A * | 12/1997 | Lackey et al. | | 623/20.32 |
| 5,876,459 A | 3/1999 | Powell | | |
| 5,879,394 A * | 3/1999 | Ashby et al. | | 623/20.33 |
| 5,906,644 A | 5/1999 | Powell | | |
| 5,957,979 A * | 9/1999 | Beckman et al. | | 623/20.33 |
| 5,964,808 A * | 10/1999 | Blaha et al. | | 623/20.28 |
| 5,997,577 A * | 12/1999 | Herrington et al. | | 623/20.15 |
| 6,004,352 A * | 12/1999 | Buni | | 623/20.33 |
| 6,126,692 A * | 10/2000 | Robie et al. | | 623/20.32 |
| 6,210,444 B1 * | 4/2001 | Webster et al. | | 623/20.33 |
| 6,210,445 B1 * | 4/2001 | Zawadzki | | 623/20.33 |
| 6,217,618 B1 * | 4/2001 | Hileman | | 623/20.33 |
| 6,299,646 B1 * | 10/2001 | Chambat et al. | | 623/20.33 |
| 6,306,172 B1 * | 10/2001 | O'Neil et al. | | 623/20.15 |
| 6,319,283 B1 * | 11/2001 | Insall et al. | | 623/20.33 |
| 6,436,145 B1 * | 8/2002 | Miller | | 623/20.34 |
| 6,485,519 B2 * | 11/2002 | Meyers et al. | | 623/20.24 |
| 6,500,208 B1 * | 12/2002 | Metzger et al. | | 623/20.28 |
| 6,506,215 B1 * | 1/2003 | Letot et al. | | 623/20.29 |
| 6,623,526 B1 * | 9/2003 | Lloyd | | 623/20.28 |
| 6,709,461 B2 * | 3/2004 | O'Neil et al. | | 623/20.33 |
| 6,916,340 B2 * | 7/2005 | Metzger et al. | | 623/20.15 |
| 6,986,791 B1 * | 1/2006 | Metzger | | 623/20.24 |
| 7,025,788 B2 * | 4/2006 | Metzger et al. | | 623/20.15 |

(Continued)

*Primary Examiner* — Alvin J. Stewart
(74) *Attorney, Agent, or Firm* — Harness, Dickey (57) ABSTRACT

A tibial prosthesis assembly can comprise a tibial tray and a tibial insert. The tibial tray can have an inferior bone engaging surface, a superior surface, and a first retaining feature. The tibial insert can have an inferior tray engaging surface, a superior bearing surface, and a second retaining feature. The first and second retaining features can cooperate to inhibit substantial lift-off of the tibial insert away from the superior surface of the tibial tray while permitting a predetermined amount of rotation of the tibial insert around the superior surface in an assembled position.

14 Claims, 5 Drawing Sheets

(56) References Cited

U.S. PATENT DOCUMENTS

| | | | |
|---|---|---|---|
| 7,070,622 B1* | 7/2006 | Brown et al. | 623/20.14 |
| 7,094,259 B2* | 8/2006 | Tarabichi | 623/20.14 |
| 7,101,401 B2* | 9/2006 | Brack | 623/20.33 |
| 7,175,666 B2 | 2/2007 | Yao | |
| 7,422,605 B2* | 9/2008 | Burstein et al. | 623/20.33 |
| 7,740,662 B2* | 6/2010 | Barnett et al. | 623/20.33 |
| 7,766,969 B2* | 8/2010 | Justin et al. | 623/20.15 |
| 8,012,215 B2* | 9/2011 | Metzger et al. | 623/20.15 |
| 8,092,546 B2* | 1/2012 | Coon et al. | 623/20.34 |
| 8,105,386 B2* | 1/2012 | Perrone et al. | 623/20.29 |
| 8,152,853 B2* | 4/2012 | Belcher | 623/20.33 |
| 8,366,781 B2* | 2/2013 | Berelsman et al. | 623/20.11 |
| 2001/0014827 A1* | 8/2001 | Chambat et al. | 623/20.33 |
| 2002/0072802 A1* | 6/2002 | O'Neil et al. | 623/20.33 |
| 2003/0093156 A1* | 5/2003 | Metzger et al. | 623/20.15 |
| 2003/0153980 A1* | 8/2003 | Brack | 623/20.33 |
| 2003/0195634 A1* | 10/2003 | Fenning et al. | 623/20.29 |
| 2004/0225368 A1* | 11/2004 | Plumet et al. | 623/20.15 |
| 2005/0246027 A1* | 11/2005 | Metzger et al. | 623/20.15 |
| 2007/0135924 A1* | 6/2007 | Verhoogen | 623/18.11 |
| 2007/0150065 A1* | 6/2007 | Angibaud | 623/20.14 |
| 2009/0125114 A1* | 5/2009 | May et al. | 623/20.14 |
| 2009/0125115 A1* | 5/2009 | Popoola et al. | 623/20.14 |
| 2010/0100189 A1* | 4/2010 | Metzger | 623/20.14 |
| 2010/0100190 A1* | 4/2010 | May et al. | 623/20.14 |
| 2010/0222890 A1* | 9/2010 | Barnett et al. | 623/20.33 |
| 2011/0202139 A1* | 8/2011 | Metzger et al. | 623/20.28 |
| 2011/0251695 A1* | 10/2011 | Lenz et al. | 623/20.15 |
| 2012/0035737 A1* | 2/2012 | Sanford et al. | 623/20.33 |
| 2012/0158152 A1* | 6/2012 | Claypool et al. | 623/20.33 |
| 2012/0265316 A1* | 10/2012 | Metzger et al. | 623/20.29 |

* cited by examiner

REVISION KNEE TIBIAL LOCKING MECHANISM

FIELD

The present disclosure relates to knee joint prosthesis and, more particularly, to a tibial prosthesis assembly having a tibial insert that is permitted to rotate a predetermined amount around a superior surface of a tibial component.

BACKGROUND

This section provides background information related to the present disclosure which is not necessarily prior art.

A knee joint prosthesis typically comprises a femoral component and a tibial component. The femoral component and the tibial component are designed to be surgically attached to the distal end of the femur and the proximal end of the tibia, respectively. The femoral component is further designed to cooperate with the tibial component in simulating the articulating motion of an anatomical knee joint. Such knee joint prostheses are generally referred to as primary knee prostheses. Knee joint prostheses, in combination with ligaments and muscles, attempt to duplicate natural knee motion as well as absorb and control forces generated during the range of flexion. In some instances however, it may be necessary to replace an existing prosthesis. Such replacement prostheses are generally referred to as revision knee prostheses. Some knee joint prostheses incorporate a tibial insert or bearing that is fixed relative to the tibial component. Such a configuration may have a very constrained tibiofemoral articulation in axial rotation. During surgery, the tibial component may be rotationally aligned with tibial landmarks. Similarly, the femoral component may be rotationally aligned with femoral landmarks. Therefore, the tibial and femoral components may be positioned independently of each other. Because they are positioned independently, the femoral component and the tibial component may not optimally align with each other. In this regard, when highly constrained articulations are forced to mate, the constrained bearing and the bone/implant interface may experience undesirable higher stresses.

SUMMARY

This section provides a general summary of the disclosure, and is not a comprehensive disclosure of its full scope or all of its features.

A tibial prosthesis assembly can comprise a tibial tray and a tibial insert. The tibial tray can have an inferior bone engaging surface, a superior surface, and a first retaining feature. The tibial insert can have an inferior tray engaging surface, a superior bearing surface, and a second retaining feature. The first and second retaining features can cooperate to inhibit substantial lift-off of the tibial insert away from the superior surface of the tibial tray while permitting a predetermined amount of rotation of the tibial insert around the superior surface in an assembled position.

According to other aspects of the present disclosure, the first retaining feature can comprise at least one post extending from the superior surface on an anterior portion of the tibial tray. The second retaining feature can comprise a vertical anterior recess that is formed in the tibial insert and that receives the at least one post. The second retaining feature can further comprise a horizontal groove defined between an inferior ledge of the tibial insert and an opposing surface of the tibial insert.

According to other features, the tibial prosthesis assembly can further comprise a locking member that selectively locates into the horizontal groove. The locking member can engage the at least one post and oppose the inferior ledge. The inferior ledge can locate intermediate the locking member and the tibial tray. The horizontal groove can be further defined by first and second bearing rotation stop surfaces. The tibial insert can be configured to rotate around the superior surface until one of the first and second bearing rotation stop surfaces engages the locking member. According to one example, the first and second bearing rotation stop surfaces can define an angle less than 180 degrees relative to each other. The first retaining feature can further comprise a posterior projection extending from the superior surface on a posterior portion of the tibial tray. The posterior portion can have an overhang that cooperates with the superior surface of the tibial tray to define a horizontal groove thereat. The second retaining feature can further comprise a horizontal flange extending from the tibial insert. The horizontal flange can be configured to locate into the horizontal channel at a location between the overhang and the superior surface of the tibial tray.

The tibial prosthesis assembly can include a tibial tray, a tibial insert, and a locking member. The tibial tray can have an inferior bone engaging surface, a superior surface, and a first retaining feature. The first retaining feature can comprise a pair of posts extending from the superior surface of an anterior portion of the tibial tray. The pair of posts can collectively define a posterior horizontal groove. The tibial insert can have an inferior tray engaging surface, a superior bearing surface, and a second retaining feature. The second retaining feature can comprise a horizontal insert groove defined between an inferior ledge and an opposing surface of the tibial insert. The locking member can selectively locate into the horizontal insert groove and the posterior horizontal groove to inhibit substantial lift-off of the tibial insert away from the superior surface of the tibial tray while permitting a predetermined amount of rotation of the tibial tray around the superior surface in an assembled position.

A tibial prosthesis assembly constructed in accordance to additional features of the present disclosure can include a tibial tray and a tibial insert. The tibial tray can have an inferior bone engaging surface, a superior surface, and a first retaining feature comprising a first indexable feature such as a female or male splined portion. The tibial insert can have an inferior tray engaging surface, a superior bearing surface, and a second retaining feature comprising a second indexable feature such as the other of the female or male splined portion. The tibial insert is configured to meshingly lock at one of a plurality of fixed rotational orientations relative to the tibial tray in an assembled position.

According to other features, the tibial tray can comprise the female splined portion and the tibial insert can comprise the male splined portion. The tibial tray can define a passage that connects an outer surface of the tibial tray with the female splined portion. The tibial prosthesis can further comprise a set screw. The set screw can be selectively advanced through the passage and into engagement with the male splined portion.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

The following description of the embodiments is specifically directed toward a tibial prosthesis having a tibial insert that incorporates a superiorly extending stabilizing post. It will be appreciated by those skilled in the art that the present disclosure is clearly not limited to tibial prostheses incorporating tibial inserts having such a geometry. Furthermore, it will be appreciated that the tibial prosthesis assembly may be used as part of a revision or a primary knee joint procedure.

Figure 1:
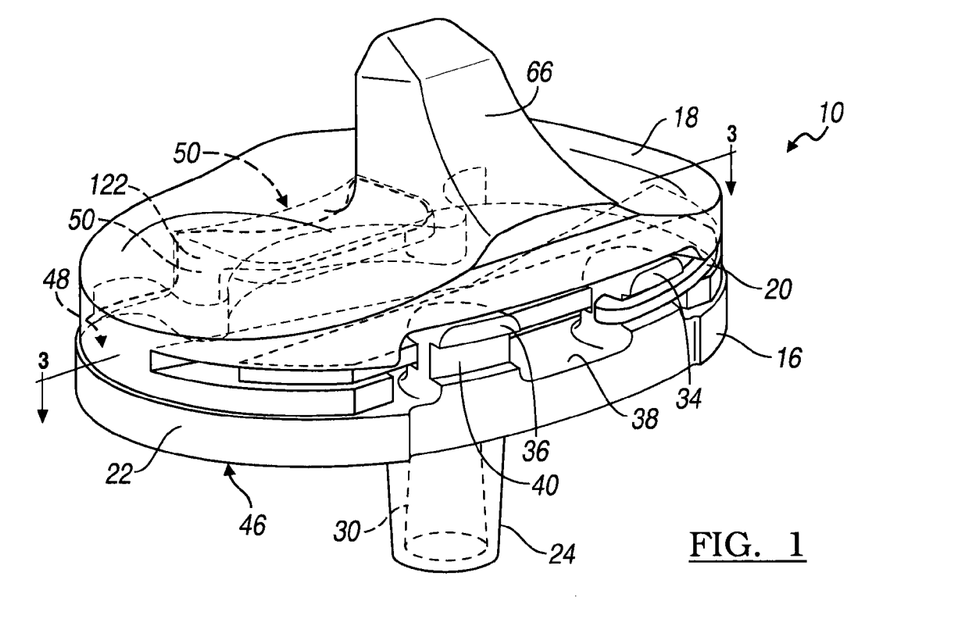
FIG. 1 is an anterior perspective view of a tibial prosthesis assembly constructed in accordance to one example of the present teachings and including a tibial component, a tibial insert, and a locking bar.
Figure 5:
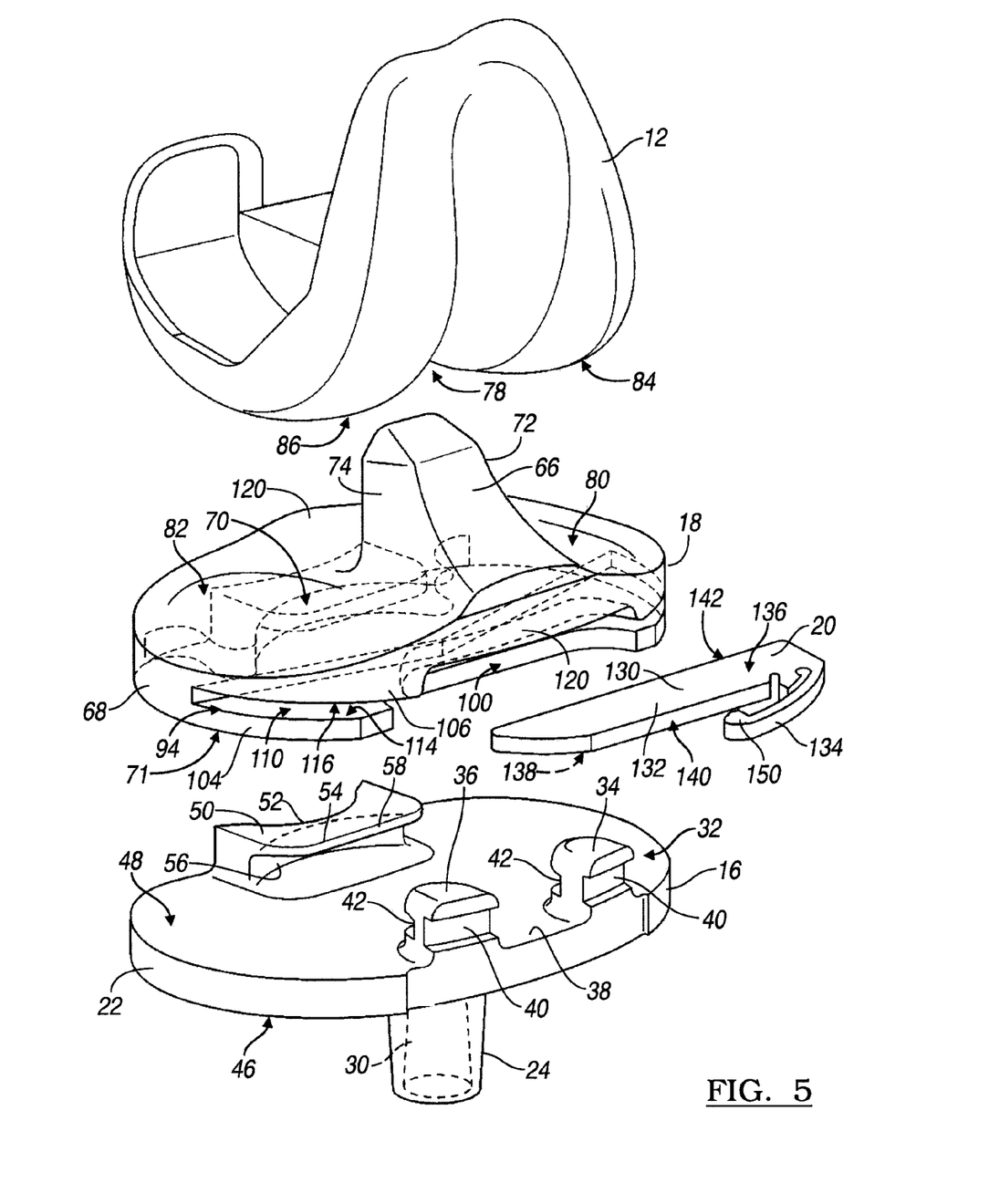
FIG. 5 is an exploded anterior perspective view of the tibial prosthesis assembly of FIG. 1.

With initial reference now to FIGS. 1 and 5, a tibial prosthesis assembly constructed in accordance to one example of the present teachings is shown and generally identified at reference numeral 10. The tibial prosthesis assembly 10 is adapted to be secured to the proximal end of a tibia after the tibia has been resected in a manner well-known in the art. Furthermore, the tibial prosthesis assembly 10 can be configured to cooperate with a complementary femoral component 12 that may be secured to the distal end of the femur after the femur has been resected in a manner which is well-known in the art.

The tibial prosthesis assembly 10 can generally include a tibial component 16, a tibial insert 18, and a locking bar 20. The tibial component 16 can include a platform-like tibial tray 22 and an inferiorly extending tibial stem 24. The tibial stem 24 is configured to be received in a corresponding opening (not shown) made by the surgeon in the longitudinal center of the tibia. A bore 30 may be disposed within the tibial stem 24 that is configured to receive a suitable support member (such as an offset stem adapter or stem extension) that may be secured to the tibia in a manner well-known in the art.

The tibial tray 22 may be formed of titanium or other suitable biocompatible material and may be constructed of different sizes having an overall medial-lateral dimension ranging from 59 mm to 91 mm. Other dimensions are contemplated.

The tibial tray 22 can further a further retaining feature 32 including a pair of integrally formed posts 34 and 36 which extend superiorly at an anterior edge 38 of the tibial tray 22. The posts 34 and 36 may be positioned equally spaced from either side of the center of the tibial component 16 in the sagittal plane. The anterior surface of each of the posts 34 and 36 includes an anterior horizontal groove 40. The posterior surface of each of the posts 34 and 36 can include a posterior horizontal groove 42. The anterior horizontal groove 40 and the posterior horizontal groove 42 cooperate to receive the locking bar 20 which is able to secure the tibial insert 18 from substantial liftoff from the tibial tray 22 while permitting a predetermined amount of rotation of the tibial insert 18 around the tibial tray 22 as will be described more fully herein.

Figure 3:
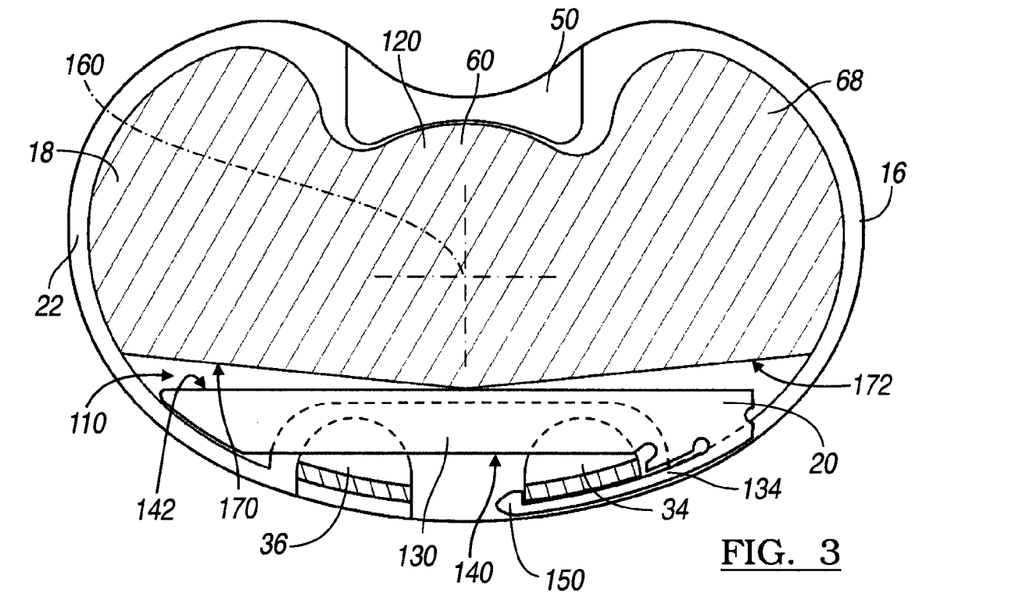
FIG. 3 is a cross-sectional view of the tibial prosthesis assembly taken along lines 3-3 of FIG. 1.
Figure 4:
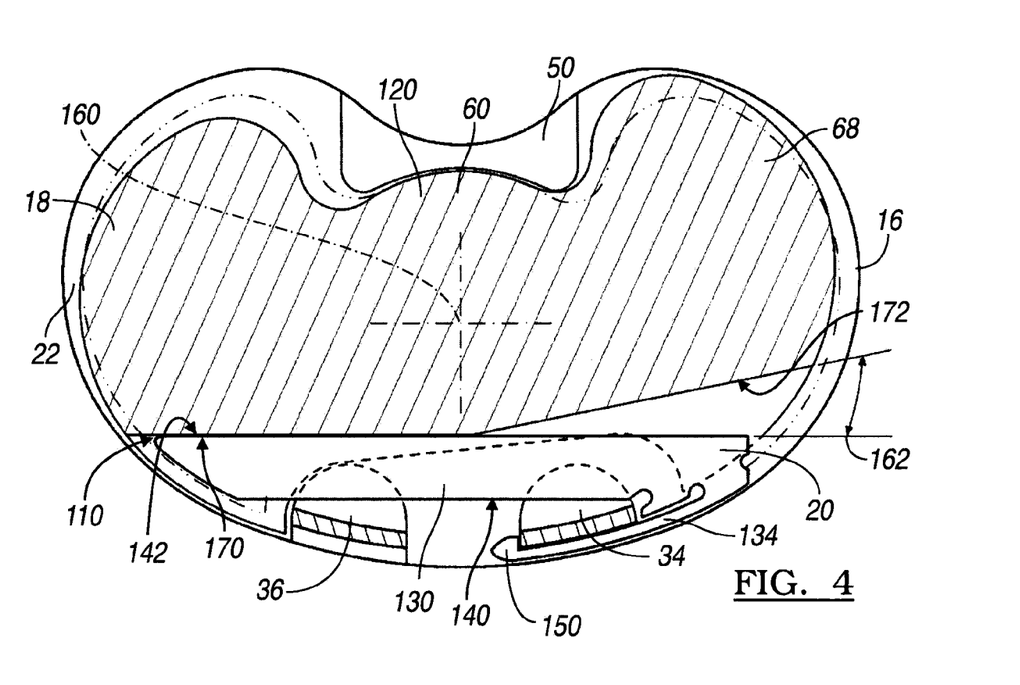
FIG. 4 is a cross-sectional superior view of the tibial prosthesis assembly of FIG. 3 and shown with the tibial insert rotated relative to the tibial component.

The tibial tray 22 can further include an inferior bone engaging surface 46 and a superior insert engaging surface 48. Disposed on the superior surface 48 of the tibial tray 22 can be a unitarily formed posterior projection 50. The posterior projection 50 can be formed as part of the first retaining feature as will become appreciated. The posterior projection 50 can extend superiorly from a posterior portion of the tibial tray 22. The posterior projection 50 can have a posterior side 52 which conforms with a corresponding posterior edge of the tibial tray 22 and an anterior side 54 which has a horizontal channel 56 formed generally between an overhang 58 of the posterior projection 50 and the superior surface 48 of the tibial tray 22. As will become appreciated herein, the horizontal channel 56 can be used to engage a horizontal flange 60 (FIGS. 3 and 6) formed in the tibial insert 18 in a manner described more fully below.

With particular reference now to FIGS. 1-5, the tibial insert 18 will be described in greater detail. The tibial insert 18 may be symmetrical about the sagittal plane in one example thereby permitting the tibial insert 18 to be used with femoral components which are designed either for the left or the right knee. In the exemplary tibial insert 18, a stabilizing post projects superiorly from a tibial insert body 68. The tibial insert body can have a superior surface 70 and an inferior tray engaging surface 71. The stabilizing post 66 can extend superiorly from the superior surface 70 of the tibial insert 18 and can include a first and a second laterally-spaced apart sides 72 and 74. The laterally-spaced apart sides 72 and 74 of the stabilizing post 66 can be positioned so as to extend into an intercondular recess 78 (FIG. 5) of the femoral component 12. Other configurations are contemplated.

Disposed on the superior surface 70 of the tibial insert 18 may be a first tibial bearing surface 80 and a second tibial bearing surface 82. The first and second tibial bearing surfaces 80 and 82 may be dish-shaped in configuration. In this regard, the first and second tibial bearing surfaces 80 and 82 may each be concavely curved in the coronal plane in a manner substantially similar to first and second femoral bearing surfaces 84 and 86 of the femoral component 12.

Figure 2:
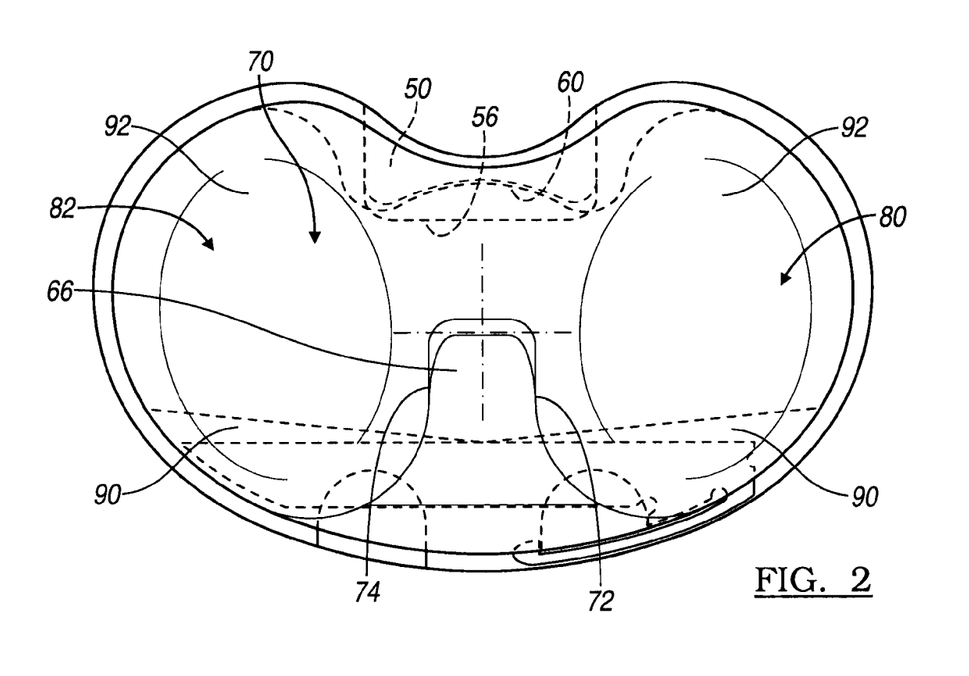
FIG. 2 is a superior view of the tibial prosthesis assembly of FIG. 1.

With particular reference now to FIG. 2, additional features of the tibial insert 18 will be described. The first and second tibial bearing surfaces 80 and 82 can each further include a first and second articulating surfaces 90 and 92. The first and second articulating surfaces 90 and 92 can be used to limit dislocation of the femoral component 12 in the sagittal plane with respect to the tibial component 16 and may be located at the anterior and posterior portions of each of the first and second tibial bearing surfaces 80 and 82. Both the articulating surfaces 90 and 92 may be concavely curved in the superior direction in the sagittal plane.

With reference now to FIGS. 1-6, the tibial insert 18 can further include a second retaining feature 94. The second retaining feature 94 can include vertical anterior recess 100 located on an anterior portion 102 of the tibial insert 18. The vertical anterior recess 100 can be configured to receive the posts 34 and 36 of the tibial tray 22. In addition, the anterior portion 102 of the tibial insert 18 can further include an inferior ledge 104 and a superior ledge 106 that cooperatively define a horizontal groove 110 therebetween. More specifically, the inferior ledge 104 has a first or upper surface 114 that opposes a second or lower surface 116 of the superior ledge 106.

The tibial insert body 68 further includes a posterior portion 120 that has a horizontal posterior recess 122 (FIG. 6) that may be adapted to receive the posterior projection 50 of the tibial tray 22 as shown in FIG. 1. The horizontal posterior recess 122 can also be formed as part of the second retaining feature 94 as will become appreciated. The horizontal posterior recess 122 incorporates the horizontal flange 60 (FIGS. 3 and 6) which is adapted to be received in the horizontal channel 56 formed in the posterior projection 50.

The locking bar 20 will now be further described. The locking bar 20 can generally comprise a main body 130 having an insertion portion 132 and a retaining portion 134. The insertion portion 132 can generally provide a first or upper surface 136 and a second or lower surface 138. The main body 130 can further include an anterior-facing surface 140 and a posterior-facing surface 142. The retaining portion 134 can further include a lobe 150 formed on a terminal end.

Figure 6:
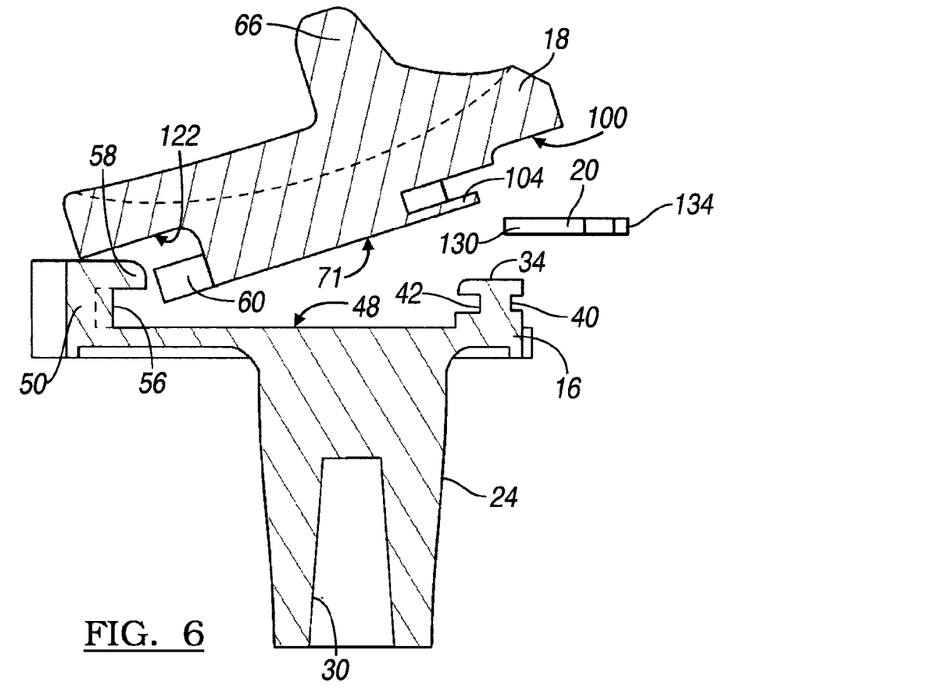
FIG. 6 is a cross-sectional view of the tibial prosthesis assembly of FIG. 5 taken along a sagittal plane and shown with the tibial insert initially positioned toward the tibial component during an assembly step.
Figure 7:
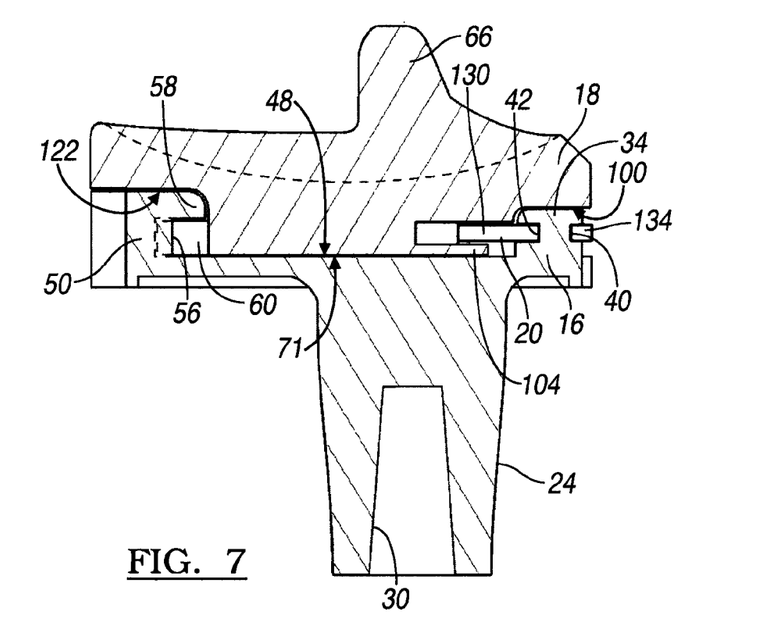
FIG. 7 is a cross-sectional view of the tibial prosthesis assembly of FIG. 6 shown subsequent to installation of the locking bar.

Assembling the tibial insert 18 to the tibial tray 22 according to one example of the present teachings will now be described. Initially, a surgeon can advance the tibial insert 18 toward the superior surface 48 of the tibial tray 22 as illustrated in FIG. 6. The horizontal flange 60 of the tibial insert body 68 can then be located generally under the overhang 58 of the posterior projection 50 such that the horizontal flange 60 locates generally into the horizontal channel 56 on the posterior projection 50 of the tibial tray 22. Next, the surgeon can generally rotate the tibial insert 18 anteriorly to the position illustrated in FIG. 7. Next, the surgeon can advance the locking bar 20 into the horizontal groove 110 of the tibial insert 18 as well as the horizontal posterior grooves 42 formed on the first and second posts 34 and 36. The locking bar 20 can be further advanced until the lobe 150 generally wraps around the post 34 as illustrated in FIG. 1. It will be appreciated that while the locking bar 20 is shown with the lobe 150 wrapped around the post 34, the locking bar 20 may alternatively be inserted from the other direction when the lobe 150 wraps around the post 36. Notably, at this time, the inferior ledge 104 of the tibial insert 18 is confined between the locking bar 20 and the superior surface 48 of the tibial tray 22 precluding substantial lift-off of the tibial insert 18 from the tibial tray 22. The tibial insert 18 however, is permitted to rotate around an axis 160 (FIG. 3) to a predetermined angle of rotation 162 (counter-clockwise, as viewed in FIG. 4, or alternatively clockwise, not specifically shown). Explained further, the tibial insert body 68 includes a first bearing rotation stop surface 170 and a second bearing rotation stop surface 172 formed at a generally posterior most end of the horizontal groove 110. The stop surfaces 170 and 172 can define an angle less than 180 degrees relative to each other.

The tibial insert 18 is free to rotate around the axis 160 until either the first bearing rotation stop surface 170 or the second bearing rotation stop surface 172 engages the posteriorly facing surface 142 of the locking bar 20. Other configurations are contemplated. For example, various tibial insert bodies 68 can be provided that have unique stop surfaces 170 and 172 that define various angles. Additionally or alternatively, various locking bars 20 can be provided that have posteriorly facing surfaces 142 that attain various opposing geometries relative to the stop surfaces 170 and 172. For example, some posterior facing surfaces 142 may have an angle less than 180 degrees. In this regard, a surgeon may intraoperatively select a tibial insert body 68 and/or a locking bar 20 that cooperate to provide a desired fixed amount of rotation of the insert 18 relative to the tibial component 16. The insert 18 therefore can be selectively indexable to a plurality of fixed (or mobile) positions or orientations relative to the tibial component 16. Again, it will be appreciated that the tibial insert 18 is inhibited from lift-off from the tibial tray 22 as the main body 130 of the locking bar 20 precludes superior advancement of the tibial insert 18 by blocking the inferior ledge 104 from superior advancement. Concurrently, the horizontal flange 60 of the tibial insert 18 can also be restricted from lift-off by the overhang 58 provided on the posterior projection 50 of the tibial tray 22. Those skilled in the art will appreciate that other configurations are contemplated where use of a locking bar 20 is not necessary. In this regard, structure on the first and second retaining members 32 and 94 may cooperate to restrict the tibial insert 18 from lift-off while permitting a predetermined amount of rotation around the axis 160.

Figure 8:
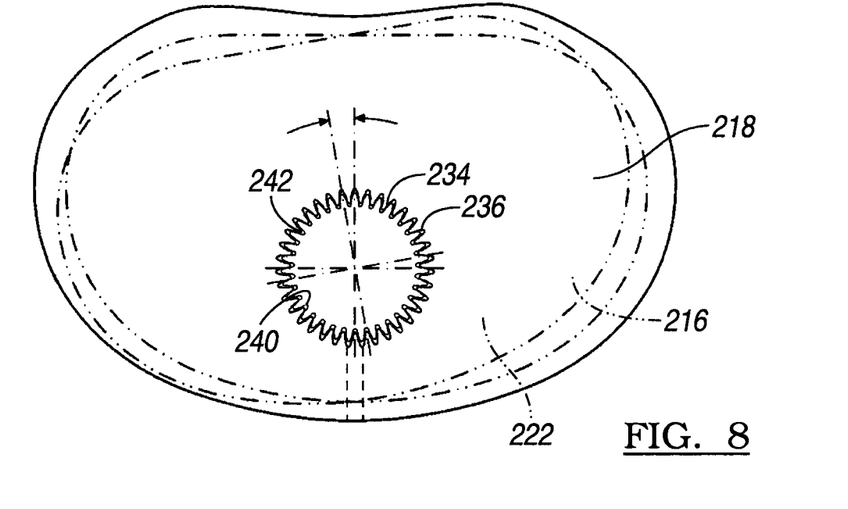
FIG. 8 is a superior view of a tibial prosthesis assembly constructed in accordance to additional features of the present teachings.
Figure 9:
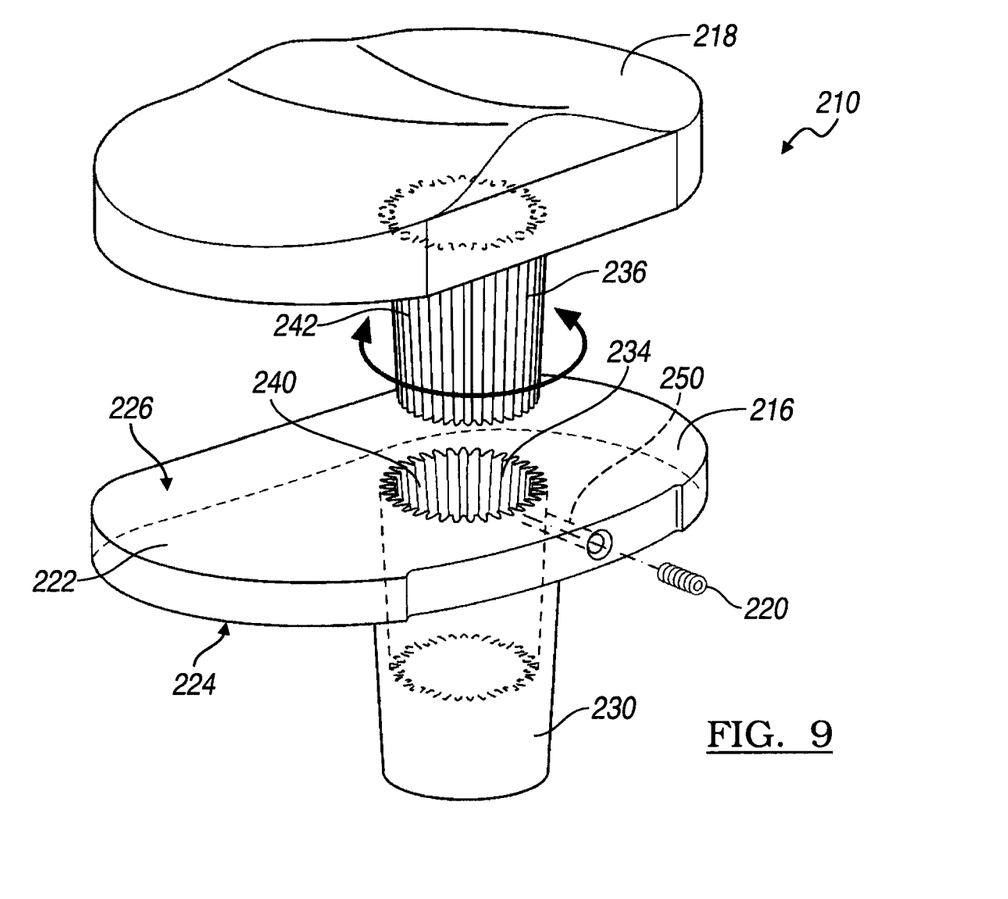
FIG. 9 is an exploded anterior perspective view of the tibial prosthesis assembly of FIG. 8.

Turning now to FIGS. 8 and 9, a tibial prosthesis assembly 210 constructed in accordance with additional features of the present teachings will be described. The tibial prosthesis assembly 210 can generally include a tibial component 216 and a tibial insert 218. The tibial prosthesis assembly 210 can optimally include a set screw 220. The tibial component 216 can generally include a platform-like tibial tray 222 having an inferior bone engaging surface 224 and a superior bearing engaging surface 226. A stem 230 can generally extend inferiorly from the tray 222. The tibial component 216 includes a first retaining or interlock feature 234 that is configured to rotatably lock with a second retaining or interlock feature 236 formed on the tibial insert 218. In the example shown, the first interlock feature 234 is in the form of female splines 240 that rotatably mesh with cooperatively formed male splines 242 formed on the second interlock feature 236 of the tibial insert 218. As can be appreciated, during assembly, a surgeon may index the second interlock feature 236 to a desired rotational orientation relative to the first interlock feature 234 and then advance the male splines 242 inferiorly into meshing engagement with the female splines 240 of the first interlock feature 234. Then, a surgeon may advance the set screw 220 through a passage 250 defined through the tibial tray 222. The set screw 220 can engage the male splines 242 and inhibit the second interlock feature 236 from lifting out of the first interlock feature 234.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A tibial prosthesis assembly comprising:
a tibial tray having an inferior bone engaging surface, a superior surface and a first retaining feature; and
a tibial insert having an inferior tray engaging surface, a superior bearing surface and a second retaining feature;
wherein the first and second retaining features cooperate to inhibit substantial lift-off of the tibial insert away from the superior surface of the tibial tray while permitting a predetermined amount of rotation of the tibial insert around the superior surface in an assembled position;
wherein the first retaining feature comprises at least one post extending from the superior surface on an anterior portion of the tibial tray; and
wherein the first retaining feature further comprises a posterior projection extending from the superior surface on a posterior portion of the tibial tray, the posterior projection having an overhang that cooperates with the superior surface of the tibial tray to define a horizontal groove thereat.

2. The tibial prosthesis assembly of claim 1 wherein the second retaining feature comprises a vertical anterior recess formed in the tibial insert that receives the at least one post.

3. The tibial prosthesis assembly of claim 2 wherein the second retaining feature further comprises a horizontal groove defined between an inferior ledge of the tibial insert and an opposing surface of the tibial insert.

4. The tibial prosthesis assembly of claim 3, further comprising a locking member that selectively locates into the horizontal groove whereby the locking member engages the at least one post and opposes the inferior ledge, wherein the inferior ledge locates intermediate the locking member and the tibial tray.

5. The tibial prosthesis of claim 4 wherein the horizontal groove is further defined by first and second bearing rotation stop surfaces, wherein the tibial insert is configured to rotate around the superior surface until one of the first and second bearing rotation stop surfaces engages the locking member.

6. The tibial prosthesis of claim 5 wherein the first and second bearing rotation stop surfaces define an angle less than 180 degrees relative to each other.

7. The tibial prosthesis of claim 1 wherein the second retaining feature further comprises a horizontal flange extending from the tibial insert, wherein the horizontal flange is configured to locate into the horizontal channel at a location between the overhang and the superior surface of the tibial tray.

8. The tibial prosthesis of claim 1, further comprising a femoral component configured to engage the tibial bearing surface.

9. A tibial prosthesis assembly comprising:
a tibial tray having an inferior bone engaging surface, a superior surface and a first retaining feature, the first retaining feature comprising a pair of posts extending from the superior surface of an anterior portion of the tibial tray, the pair of posts collectively defining a posterior horizontal groove;
a tibial insert having an inferior tray engaging surface, a superior bearing surface and a second retaining feature, the second retaining feature comprising a horizontal insert groove defined between an inferior ledge and an opposing surface of the tibial insert; and
a locking member that selectively locates into the horizontal insert groove and the posterior horizontal groove to inhibit substantial lift-off of the tibial insert away from the superior surface of the tibial tray while permitting a predetermined amount of rotation of the tibial tray around the superior surface in an assembled position.

10. The tibial prosthesis of claim 9 wherein the horizontal groove is further defined by first and second bearing rotation stops surfaces, wherein the tibial insert rotates around the superior surface until one of the first and second bearing rotation stop surfaces engages the locking member.

11. The tibial prosthesis of claim 10 wherein the first and second bearing rotation stop surfaces define an angle less than 180 degrees relative to each other.

12. The tibial prosthesis assembly of claim 9 wherein the first retaining feature further comprises a posterior projection extending from the superior surface on a posterior portion of the tibial tray, the posterior portion having an overhang that cooperates with the superior surface of the tibial tray to define a horizontal groove thereat.

13. The tibial prosthesis of claim 12 wherein the second retaining feature further comprises a horizontal flange extending from the tibial insert, wherein the horizontal flange is configured to locate into the horizontal channel at a location between the overhang and the superior surface of the tibial tray.

14. The tibial prosthesis of claim 9, further comprising a femoral component configured to engage the tibial bearing surface.

* * * * *